United States Patent [19]
Honig et al.

[11] 3,954,917
[45] May 4, 1976

[54] METHOD OF PREPARING STABLE CONDENSATION PRODUCTS USING AN ALCOHOL-ALKYLENE OXIDE TREATMENT AND PRODUCTS THEREFROM

[75] Inventors: Milton L. Honig, New York; Edward N. Walsh, New City, both of N.Y.

[73] Assignee: Stauffer Chemical Company, Westport, Conn.

[22] Filed: May 28, 1974

[21] Appl. No.: 473,470

[52] U.S. Cl. .......................... 260/928; 260/2.5 AJ; 260/978
[51] Int. Cl.² .......................... C07F 9/08; C08J 9/00
[58] Field of Search .......................... 260/928, 978

[56] References Cited
UNITED STATES PATENTS

| | | | |
|---|---|---|---|
| 3,641,202 | 2/1972 | Biranowski et al. | 260/928 X |
| 3,822,327 | 7/1974 | Weil | 260/928 |

*Primary Examiner*—Anton H. Sutto
*Attorney, Agent, or Firm*—Richard P. Fennelly

[57] ABSTRACT

Products which are phosphorus containing oligomers having

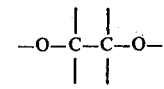

linkages between phosphorus atoms and which are obtained by the self-condensation of β-haloalkyl esters of pentavalent phosphorus acids or by condensation of these esters with an alkyl ester of a pentavalent phosphorus acid are treated with an alcohol having the formula ROH wherein R is a $C_1$–$C_{20}$ alkyl group or a substituted alkyl group and then with an alkylene oxide for a period of time after residual acidity has been neutralized, e.g., by treatment with an alkylene oxide, which is sufficient to enable the alcohol and the alkylene oxide to act upon labile groups contained in the condensed product and to neutralize any further acidity generated by the opening of such groups. The stabilized product formed by this process when incorporated in a polyurethane foam gives a foam having superior green strength to a foam containing a condensed oligomer which is not so treated.

9 Claims, No Drawings

METHOD OF PREPARING STABLE CONDENSATION PRODUCTS USING AN ALCOHOL-ALKYLENE OXIDE TREATMENT AND PRODUCTS THEREFROM

TECHNICAL DESCRIPTION OF THE INVENTION

The present invention is a process for forming an improved condensation product β-haloalkyl esters of pentavalent phosphorus acids which have flame retardant properties. A number of processes for formation of the class of compounds of interest herein are described in the patent literature and in copending applications including the following:

1. U.S. Pat. No. 3,513,644 to Edward D. Weil which describes the preparation of polycondensed oligomeric phosphates by heating of tris(2-haloalkyl) phosphates.

2. U.S. Pat. Nos. 3,641,202 and 3,695,925 to Edward D. Weil which describe the preparation of oligomeric polycondensed phosphonates from bis(haloalkyl) vinyl phosphonates.

3. U.S. Pat. No. 3,866,187 of Edward D. Weil which describes liquid poly(haloethylethyleneoxy) phosphoric acid esters prepared by condensing tris(2-haloethyl)phosphate.

4. U.S. Ser. No. 410,583, filed Nov. 12, 1973 and U.S. Pat. No. 3,855,359 of Edward D. Weil which describe the copolycondensation of certain phosphates and phosphonates having a 2-haloalkyl group on at least one of these reactants.

5. U.S. Pat. No. 3,822,327 to Edward D. Weil which describes homo- and copolycondensates of bis(2-haloethyl) vinylphosphonates.

6. U.S. Pat. No. 3,891,727 of Edward D. Weil which relates generally to condensation products of haloalkyl esters of pentavalent phosphorus acids.

These patents and disclosures insofar as they relate to the condensation products usable in the practice of the instant invention are incorporated herein by reference.

The process of this invention is particularly applicable to the homocondensation product of tris(2-chloroethyl) phosphate, to the copolycondensation product of bis(2-chloroethyl) vinylphosphonate and dimethyl methylphosphonate, to the copolycondensation product of bis(2-chloroethyl) vinylphosphonate and trimethyl phosphate, to the homopolycondensation product of bis (2-chloroethyl) vinylphosphonate, and to the copolycondensation product of tris(2-chloroethyl)-phosphate and dimethyl methylphosphonate.

Briefly, the polycondensation products are produced by reacting the monomer (both of which, as has already been noted, may be the same) to give off a volatile alkyl halide or alkylene dihalide and leave behind a nonvolatile oligomeric condensation product.

The polycondensation reaction can be run without a catalyst, but, to permit lower temperatures and/or shorter reaction times, it is preferably conducted in the presence of a nucleophilic catalyst. Suitable quantities of catalyst are from a few parts per million, e.g., 50 p.p.m., up to about 10% by weight, preferably 0.01–5% based on weight of the reaction mixture.

The reaction mixture, with proper amount of catalyst, if desired, and in the desired molar ratio of starting materials, is heated to a temperature within the range of from about 110° to about 250°C., preferably 160°–180°C. Further details concerning the condensation reaction may be found in the disclosures previously incorporated herein by reference.

It has been suggested in U.S. Pat. No. 3,866,187 of Edward D. Weil, in Canadian Pat. No. 908,186, and in Belgian Pat. No. 789,815, that residual acidity in the type of product of interest herein could be removed by treatment with an alkylene oxide neutralizing agent until acidic groups in the product, i.e., the residual acid content, are present to an insignificant degree. Alternatively, it has been suggested in U.S. Pat. No. 3,891,727 of Edward D. Weil that treatment with an alcohol or water and then with an epoxide be utilized. However, there was no suggestion in these prior art patents of using an alcohol and an alkylene oxide treatment after neutralization had been accomplished for an additional length of time to allow the alcohol and alkylene oxide to act upon labile groups contained in the condensed product, e.g., pyro, cyclic, and bridged groups, and thereby neutralize any further acidity which would occur by the opening of said groups. This invention is particularly directed to continuing the treatment with an alcohol and an alkylene oxide until labile groups, such as cyclic, pyro and bridged groups, have been opened and neutralized.

The treatment of the polycondensed product after it has been neutralized of residual acidity, e.g., by treatment with an alkylene oxide for 3–8 hours at 90°–110°C., is carried out at temperatures of 20° to 180°C, preferably 50°C to 150°C with an alcohol having the formula ROH where R is alkyl of from 1 to 20 carbon atoms and is either unsubstituted or substituted. The time of treatment is 2–4 hours. The amount which is used varies between 1% and 10% by weight of the product.

As the group R in the alcohol, any alkyl or substituted alkyl group can be used so long as the substituent or substituents do not adversely affect the ring-opening reactions and do not cause undesirable side reactions, e.g. reactions with portions of the polycondensation product which would result in a loss of or reduction in fire-retardant properties. Usable substituents thus include aryloxy, halogen, alkoxy, alkenyl, aryl, acyl, acyloxy, hydroxy, amido, alkylthio, arylthio, carbalkoxy, carboxamido, cyano and nitro. Suitable alcohols are exemplified by methanol, ethanol, n-butyl alcohol, lauryl alcohol, other monohydric alkanols having up to 20 carbon atoms, allyl alcohol, 2,3-dibromopropanol, tribromoneopentyl alcohol, dibromoneopentylene glycol, ethylene glycol, dibromobutenediol, diethylene glycol, methoxyethanol, ethoxyethanol, butoxyethanol, 2-chloroethanol, benzyl alcohol, glycerol, pentaerythritol, dipentaerythritol, trimethylolethane, trimethylolpropane, sorbitol, glucose, sucrose, lactose, methylglucoside and polyoxyalkylated (especially polyoxyethylated or polyoxypropylated) derivatives of any of the aforementioned polyols, acryloxyethanol, carbamyloxyethanol, acetoxyethanol, methacryloxyethanol, N-hydroxymethylacrylamide, vinyl hydroxyethyl ether, methylolamines, methylolureas, and hydroxymethylphenols.

After the alcohol treatment has occurred the product is treated with an alkylene oxide. "Alkylene oxide" is therefore broadly intended to include any compound having an oxirane group

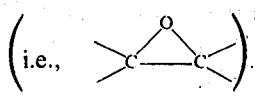

Illustrative of these compounds are ethylene oxide, propylene oxide, butylene oxide, styrene oxide, epichlorohydrin, epibromohydrin, diglycidyl ether, glycidyl butyl ether, glycidyl alkyl ether, glycidyl ether of phenol, diglycidyl ether of resorcinol, glycidyl ether of cresol and brominated cresol, glycidyl esters of acids such as acetic, acrylic and methacrylic acid, glycidol, diglycidyl ethers of bisphenol A and related epoxy resins made from bisphenol, or tetrahalobisphenols and epichlorohydrin, the diepoxide of dicyclopentylene ether, the diepoxide of vinylcyclohexene, the diepoxide of cyclohexenylmethyl cyclohexenecarboxylate, diepoxide of bis(cyclohexenylmethyl) adipate, and the like. The alkylene oxide that is added after the alcohol treatment is used in an amount sufficient to neutralize acidic structures formed by the action of the alcohol on labile structures in the product. This amount is generally from about 1 to about 10% by weight based on the total weight of the product. When a gaseous epoxide, such as ethylene oxide, is employed, it may conveniently be passed in and through the reaction product until the acidity formed by opening the labile groups has been neutralized. This will generally involve treating the product for about 1–8 hours, preferably from about 4–6 hours. The unreacted excess which passes through can, if desired, be collected and recycled. The treatment with alkylene oxide is performed at a temperature of about 60°–140°C., preferably 90°–110°C.

The product formed by the process described herein when incorporated in a polyurethane foam formulation will give a foam which possesses superior green strength to a foam containing a phosphorus oligomer that is not treated in accordance with this invention. Poor green strength is demonstrated by a tacky top surface on the foam and/or a foam which tears easily after the initial cure.

The following working Examples illustrate the invention:

EXAMPLE I

A polycondensed tris(2-chloroethyl) phosphate was formed by heating the tris(2-chloroethyl)phosphate in the presence of 0.2% $Na_2CO_3$ at 165°C. This product was neutralized by treatment with ethylene oxide for about 3.3 hours. The acid number was 0.90 mg KOH/g of product. It was determined by treating a 10g sample with 10 ml of water in 20 ml of acetone and titrating this with 0.1 N KOH after stirring the mixture for 20 minutes. The value indicates neutralization of free acidity. The acid number after allowing a similar 10g sample in 10 ml of water and 20 ml of acetone after 24 hours stirring at room temperature was 7.62 mg KOH/g. This indicated the latent acid content. Subsequently, 1129 g of this material and 56g of ethanol were heated together for three hours at 95°–100°C. Excess ethanol was then removed by vacuum distillation. The resultant product showed a latent acid number of 6.22, according to the second procedure mentioned above, and was used in the following Examples.

EXAMPLE II

A 200g portion of the product from Example I was taken and was heated at 80°–130°C. with 2g of the diepoxide of cyclohexenylmethyl cyclohexene carboxylate (Union Carbide "ERL 4221") for about 3 hours.

EXAMPLE III

Another 200g portion of the product from Example I was treated for 9 hours with ethylene oxide at about 100°C. Thereafter, residual volatiles were stripped under vacuum. A latent acid number of 5.0 mg KOH/g was obtained.

EXAMPLE IV

The ethylene oxide neutralized polycondensation product of tris(2-chloroethyl) phosphate was charged into a reactor with 30g of ethanol and was heated at 90°–100°C. for about 3 hours. Excess ethanol was then removed under vacuum. Ethylene oxide was then added at about 80°–100°C. for about 6½ hours.

EXAMPLE V

The products from Examples I–III were incorporated in a polyurethane foam formulation at 10 parts by weight. The other ingredients were:

| REAGENT | PARTS BY WEIGHT |
|---|---|
| Niax 16-46 Polyol (Union Carbide) | 100 |
| $H_2O$ | 4 |
| Niax A-1 Catalyst | 0.1 |
| N-ethyl morpholine | 0.2 |
| L-548 Silicone | 1.0 |
| T-10 Stannous Octoate (50% in dioctyl phthalate) | 0.4 |
| Toluene Diisocyanate (80% 2,4 isomer; 20% - 2,6 isomer) | 51.0 |

The foam was cured for 10 minutes at 125°C. and was examined for its physical properties. The Table below sets forth the green strength of the foam. Green strength is a measure of the proper gelation and easily handling characteristics. Poor green strength is demonstrated by a tacky top surface on the foam and/or a foam structure which tears easily after the initial cure. Condensed products that are not treated in accordance with the present invention demonstrate such inferior physical properties:

| PRODUCT | GREEN STRENGTH |
|---|---|
| Example II | Good |
| Example III | Excellent |
| Control* | Poor |

*Polycondensed tris (2-chloroethyl) phosphate which was formed as set forth in Example I and which was only treated to an ethylene oxide neutralization procedure for about 3 hours.

The condensation products of a β-haloalkyl ester of a pentavalent phosphorus acid which are meant to be included herein are those formed by self-condensation of such esters or of condensation of such an ester with other alkyl esters of pentavalent phosphorus acids. In addition to the particular condensation products described above, this definition also includes the type of condensation products described in U.S. Pat. No. 3,764,640 to Klose.

What is claimed is:

1. A process for forming a stabilized condensation product of a β-haloalkyl ester of a pentavalent phosphorus acid which is adapted to be incorporated in a polyurethane foam which comprises treating said product after it has had its residual acidity neutralized by treatment with an alkylene oxide with between 1 and 10% by weight of an alcohol having the formula ROH, where R is a $C_1$–$C_{20}$ alkyl group or a $C_1$–$C_{20}$ alkyl group containing a substituent which does not result in a reduction of fire-retardant properties for the stabilized product for a period of from 2 to 4 hours at 20° to 180°C., and thereafter treating said product with about 1% to about 10% by weight of an alkylene oxide for about 1 to 8 hours at a temperature of about 60° to 140°C.

2. A stabilized condensation product of a β-haloalkyl ester of a pentavalent phosphorus acid which is formed by the process of claim 1.

3. A product as claimed in claim 2 wherein the stabilized condensation product is stabilized polycondensed tris(2-chloroethyl)phosphate.

4. A process as claimed in claim 1 wherein the alkylene oxide is added for a period of about 4–6 hours.

5. A process as claimed in claim 1 wherein the alkylene oxide is added at a temperature of about 90°–110°C.

6. A process as claimed in claim 1 wherein the alkylene oxide which is added is ethylene oxide.

7. A process as claimed in claim 1 wherein the alcohol is added at a temperature of 50° to 150°C.

8. A process as claimed in claim 1 wherein the alcohol is ethanol.

9. A process as claimed in claim 1 wherein the stabilized condensation product is stabilized polycondensed tris(2-chloroethyl)phosphate.

* * * * *